United States Patent
Kelly et al.

(10) Patent No.: US 10,716,545 B2
(45) Date of Patent: Jul. 21, 2020

(54) ULTRASOUND SYSTEM FOR IMAGING AND PROTECTING OPHTHALMIC OR OTHER SENSITIVE TISSUES

(71) Applicant: FUJIFILM SonoSite, Inc., Bothell, WA (US)

(72) Inventors: Gina Kelly, Bothell, WA (US); Andrew Lundberg, Woodinville, WA (US); Keith Williams, Seattle, WA (US); Lee D. Dunbar, Loon Lake, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 485 days.

(21) Appl. No.: 15/389,428

(22) Filed: Dec. 22, 2016

(65) Prior Publication Data

US 2018/0177495 A1 Jun. 28, 2018

(51) Int. Cl.
- *A61B 8/00* (2006.01)
- *A61B 8/10* (2006.01)
- *A61B 8/08* (2006.01)
- *A61B 8/14* (2006.01)

(52) U.S. Cl.
CPC ............. *A61B 8/58* (2013.01); *A61B 8/10* (2013.01); *A61B 8/14* (2013.01); *A61B 8/5207* (2013.01); *A61B 8/54* (2013.01); *A61B 8/0866* (2013.01)

(58) Field of Classification Search
None
See application file for complete search history.

(56) References Cited

U.S. PATENT DOCUMENTS

| | | | |
|---|---|---|---|
| 9,320,427 B2 * | 4/2016 | Levien | A61B 3/102 |
| 2003/0097065 A1 | 5/2003 | Lee et al. | |
| 2006/0058671 A1 | 3/2006 | Vitek et al. | |
| 2011/0196236 A1 | 8/2011 | Swamy et al. | |
| 2014/0049748 A1 | 2/2014 | Hee | |
| 2016/0082293 A1 | 3/2016 | Koskela et al. | |

OTHER PUBLICATIONS

Barnett et al. The sensitivity of biological tissue to ultrasound. Ultrasound Med Biol 1997; 23(60: 805-12 (Year: 1997).*
International Searching Authority, International Search Report and Written Opinion, PCT Patent Application PCT/US2017/067103, dated Mar. 30, 2018, 13 pages.

* cited by examiner

Primary Examiner — Brian T Gedeon
(74) Attorney, Agent, or Firm — Womble Bond Dickinson (US) LLP

(57) ABSTRACT

An ultrasound imaging system includes a processor programmed to identify the type of tissue being imaged and to confirm that one or more system settings and/or the energy of ultrasound imaging signals delivered is set appropriately for such tissue. In one embodiment, an image obtained with the ultrasound imaging system is analyzed to determine if the tissue is ophthalmic (eye) tissue. If so, the system parameter settings and/or the transmit power of the signals produced by the ultrasound system are adjusted or maintained at a level that is appropriate for imaging such tissue.

17 Claims, 4 Drawing Sheets

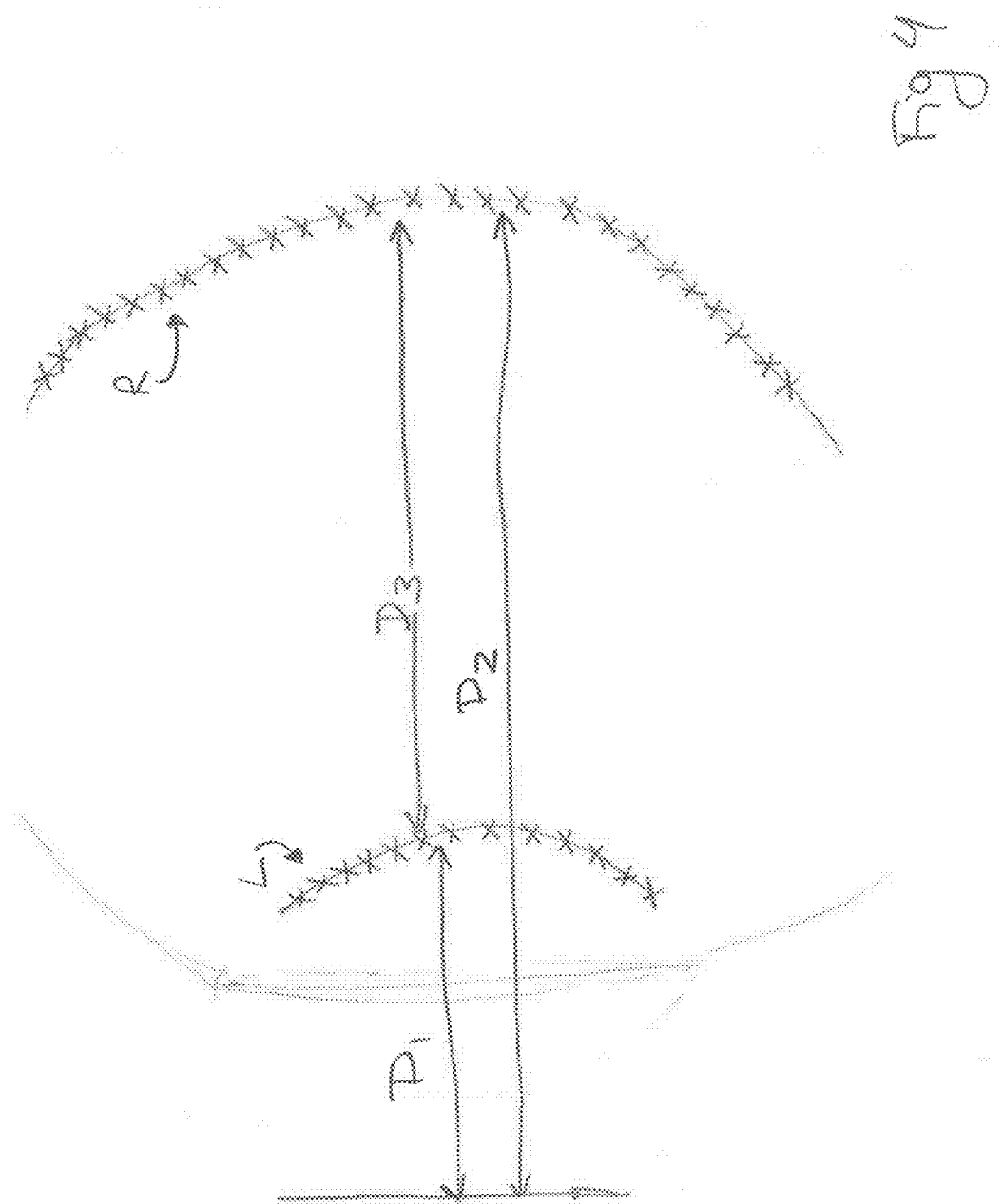

ULTRASOUND SYSTEM FOR IMAGING AND PROTECTING OPHTHALMIC OR OTHER SENSITIVE TISSUES

TECHNICAL FIELD

The disclosed technology relates to ultrasound imaging systems and in particular to ultrasound imaging systems that are useful in imaging ophthalmic or other sensitive tissues.

BACKGROUND

Ultrasound is becoming an increasingly used, non-invasive imaging technique for examining ophthalmic (e.g. eye) tissue to asses tissue health, trauma or disease. With ultrasound imaging, high frequency acoustic waves are transmitted into the tissue and the corresponding echo signals are detected and analyzed. One or more characteristics of the echo signals such as their amplitude, phase and frequency shift are analyzed and represented in an image of the tissue.

One potential danger with ultrasound imaging is if the energy delivered into the tissue is great enough to cause heating of the tissue and/or cavitation in fluids. These effects are particularly dangerous when ultrasound signals are applied to the eye.

While most ultrasound operators are trained to apply a safe level of ultrasound energy to ophthalmic or other sensitive tissues, such examinations may be performed on the battlefield, at accident sites or in otherwise chaotic situations where mistakes can be made. In addition, human error may cause an operator to forget to set the transmit power of an ultrasound imaging system to the appropriate level before examining sensitive tissue.

BRIEF DESCRIPTION OF THE DRAWINGS

FIG. 4 illustrates measurements that can be obtained from an ultrasound image in order to determine whether the image represents ophthalmic tissue.

DETAILED DESCRIPTION

As will be explained in further detail below, the disclosed technology relates to improvements in ultrasound imaging systems and in particular to an ultrasound imaging system that reduces the likelihood that excess acoustic energy will be delivered to sensitive tissues such as ophthalmic tissue. In one embodiment, a processor is programmed to analyze an ultrasound image to determine if the tissue being imaged is likely ophthalmic tissue. If so, the processor acts to produce an alert that prompts an operator to confirm that the settings for the ultrasound machine are appropriate for this type of tissue and/or that the acoustic energy produced is within an acceptable range. In another embodiment, the processor is programmed to confirm that the settings are appropriate and/or that the acoustic energy of the signals produced is within a safe range for ophthalmic tissue before a scan begins. In one embodiment, the ultrasound system obtains an image of the tissue and the processor is configured to analyze the image to determine if the tissue is not ophthalmic or other sensitive tissue. If the tissue is not ophthalmic tissue, then the system settings and/or acoustic energy produced can be changed either under program control or by an operator. Other embodiments are also disclosed.

Figure 1:
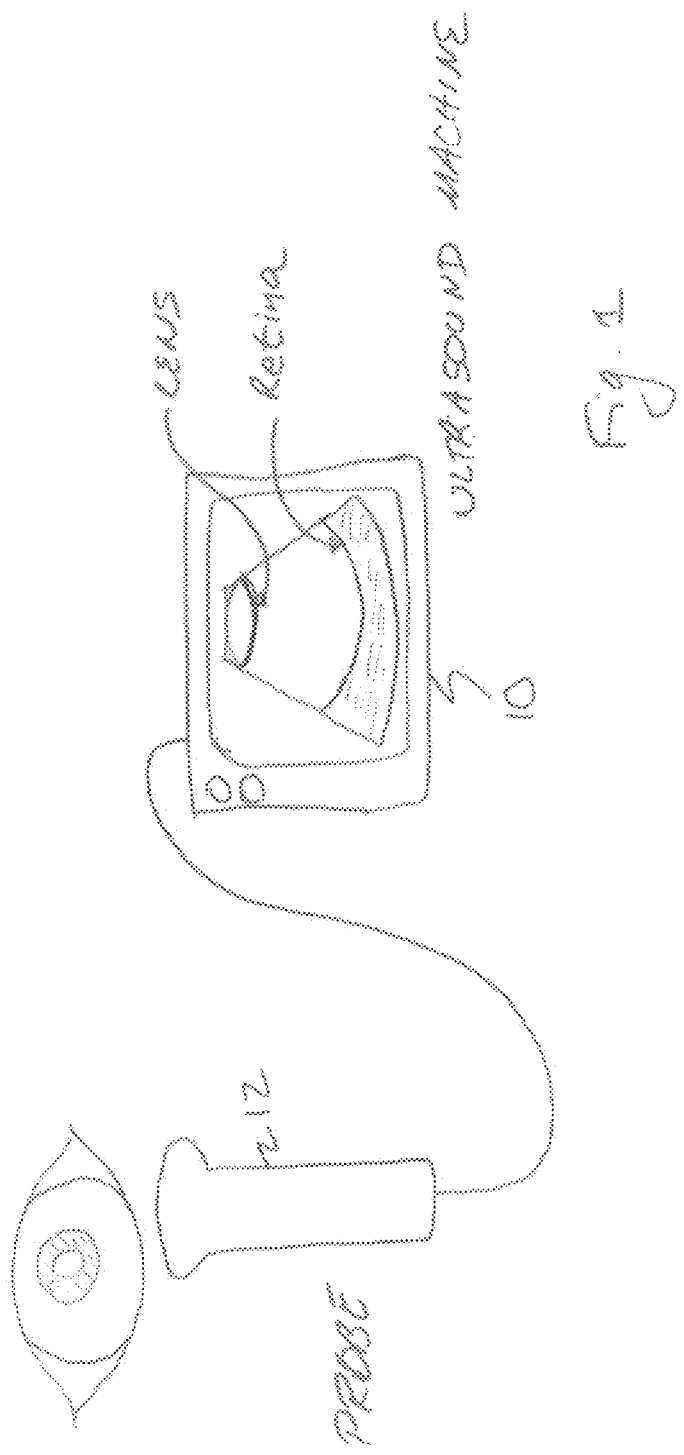
FIG. 1 is a simplified diagram of an ultrasound imaging system for obtaining and displaying images of ophthalmic tissue in accordance with one embodiment of the disclosed technology.

FIG. 1 shows an exemplary ultrasound imaging system that implements the disclosed technology for imaging an eye of a patient. In the embodiment disclosed, an ultrasound imaging system 10 can be a hand held, portable or cart-based system that uses a transducer probe 12 to transmit ultrasound signals into a region of interest and to receive the corresponding echo signals in order to produce an image of the tissue being scanned. The probe 12 can include a single element transducer that is mechanically moved to sweep the transducer over a range of beam angles. Alternatively, the probe 12 can include a one or two dimensional phased array that can selectively change the transmit and receive beam angles electronically.

The ultrasound imaging system 10 operates to convert the received echo signals into an image that can be viewed by an operator, stored electronically for digital record keeping or transmitted via a wired or wireless communication link to another device or location. In accordance with some embodiments of the disclosed technology, the ultrasound imaging system includes a processor that is programmed to determine if the tissue being imaged is likely ophthalmic tissue for which the energy of the ultrasound signals delivered should be selected to be in a range that is safe for such tissue.

In some embodiments, a processor in the ultrasound imaging system uses image recognition technology to determine if an image produced by the system likely represents ophthalmic tissue. If so, the system settings and/or transmit energy is checked to confirm they are safe for imaging such tissue. If the settings are wrong or the transmit energy is too high, the processor is programmed to change the settings or turn down the transmit level or to alert the user to select an appropriate imaging state that is safe for ophthalmic imaging. In an alternate embodiment, the system settings are set for sensitive tissues and/or the transmit energy of the ultrasound system is limited until the processor can determine that the tissue being imaged is not a sensitive tissue. Once it is determined that the tissue is not ophthalmic or other sensitive tissue, the system settings and/or transmit energy level can be increased either by the processor or by an operator.

In still other embodiments, the transducer probe can include a small imaging camera similar to those found on cellular telephones. Imagines captured by the camera as the probe is being used, or is about to be used, are analyzed by the processor to determine the type of tissue being examined. If the images indicate that the tissue is ophthalmic tissue, the processor in the ultrasound system can produce an alert or set the system settings and/or transmit energy of the ultrasound signals delivered to be within a safe range.

Figure 2:
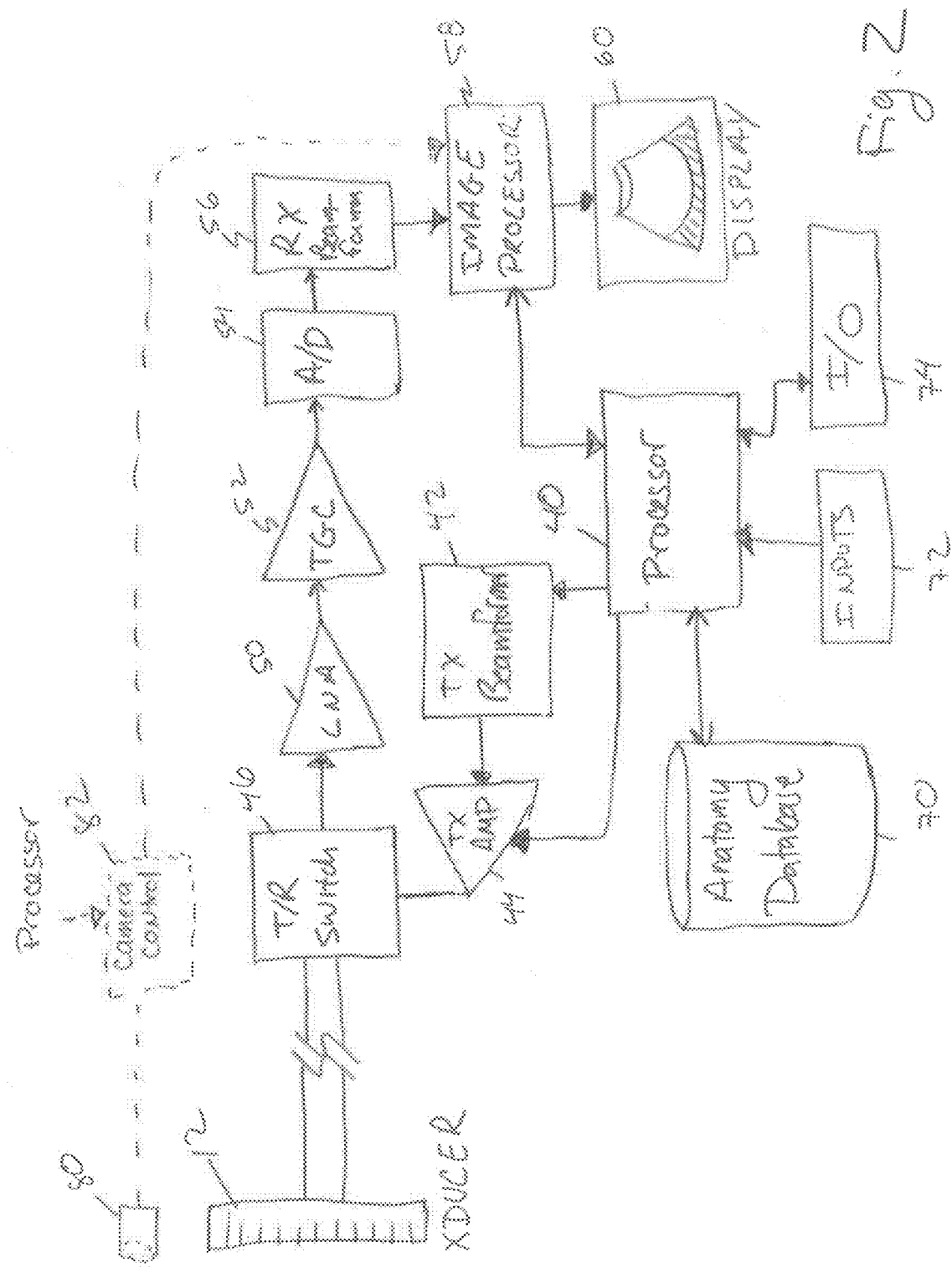
FIG. 2 is a block diagram of an ultrasound imaging system in accordance with an embodiment of the disclosed technology.

FIG. 2 shows a simplified block diagram of an ultrasound imaging system in accordance with an embodiment of the disclosed technology. As will be appreciated by those skilled in the art, the ultrasound system may be constructed with components that are different than those shown. In addition, the ultrasound system includes components that are not discussed (e.g. a power supply etc.) and that are not necessary for an understanding of how to make and use the disclosed technology. In the embodiment shown, the ultrasound system includes processor 40 having a built-in or external memory (not shown) containing instructions that are executable by the processor to operate the ultrasound imaging system as will be explained in detail below. In the transmit path, the ultrasound system includes a transmit beamformer 42, a transmit gain control amplifier 44 and a transmit/receive switch 46. If the ultrasound probe 12, is a phased array type, the transmit beamformer 42 operates to generate a number of signals having a relative amplitude and phase (timing) selected to produce an ultrasound beam from the transducer elements of the probe that constructively adds in a desired direction (the desired beam angle). The signals from the transmit beamformer are amplified by the transmit amplifier 44 to a sufficiently high voltage level that will cause the transducer elements to produce the desired acoustic signals in the tissue being examined.

In some embodiments, the processor 40 is connected to supply a control command such as a digital value of 0-255 to the transmit gain control amplifier to control the amount of energy in the signals produced. The manner in which the energy of the ultrasound signals is varied can include controlling the voltage rails (+V, −V) on the transmit amplifier 44 or changing one or more of the amplitude or duty cycle of the signals produced or supplying the signals to a varying number of transducer elements that transmit the signal pulses.

The amplified transmit signals are supplied to the transducer probe 12 through the transmit/receive switch 46, which disconnects or shields sensitive receive electronics from the transmit signals at the time they are delivered to the transducer probe 12. After the signals are transmitted, the transmit/receive switch 46 changes positions and connects the receive electronics to the transducer elements to detect the corresponding electronic echo signals created when the returning acoustic waves impinge upon the transducer elements.

In the receive path, the ultrasound imaging system includes a low noise amplifier 50, a time gain control (TGC) amplifier 52, an analog to digital converter 54, a receive beamformer 56 and an image processor 58. Analog echo signals produced by the imaging probe are directed through the transmit/receive switch 46 to the low noise amplifier where they are amplified. The TGC amplifier 52 applies a variable amplification to the received signals according to the return time of the signals (e.g. proportional to the depth in the tissue being imaged to counteract the attenuation of the signals versus depth). The amplified signals are then converted into a digital format by the analog to digital converter 54. The digitized echo signals are then delayed and summed by the receive beamformer 56 before being supplied to the image processor.

Images produced by the image processor 58 from the received signals are displayed on a display 60. In addition, the images can be recorded in an image memory (not shown) for future recall and review. A number of inputs 72 are provided to allow an operator to change the operating parameters of the ultrasound imaging system and to enter data such as the patient name or other record keeping data. In addition, the ultrasound imaging system includes input/output (I/O) circuitry to allow the system to connect to computer communication links (LAN, WAN, Internet etc.) through a wired (e.g. Ethernet, USB, Thunderbolt, Firewire, or the like) or wireless (802.11, cellular, satellite, Bluetooth or the like) communication link. I/O circuitry can also include one or more speakers for communicating with a user.

The details of the components that comprise the ultrasound imaging system and how they operate are generally considered to be well known to those of ordinary skill in the art. Although the ultrasound imaging system is shown having many separate components, it will be appreciated that devices such as ASICs or digital signal processors (DSPs) may be used to perform the function of multiple ones of these individual components.

As discussed above, the processor 40 is programmed to lessen the likelihood that high power ultrasound signals will be applied to sensitive tissues such as the eye. In one embodiment, when the tissue being examined is ophthalmic tissue, the processor is programmed to generate an alert to the operator to check the system settings or to control the energy delivered so that the tissue being examined is unlikely to be damaged by the ultrasound signals. Although the disclosed technology is described in the context of limiting the amount of energy delivered to ophthalmic tissues, the technology can also be used to limit the amount of energy delivered to a fetus or other sensitive tissues.

In one embodiment, the processor 40 is programmed to analyze images produced by the image processor 58 to determine if the image represents ophthalmic tissue or other sensitive tissue for which the energy delivered to the tissue should be limited. In another embodiment, the processor analyzes images produced by the image processor 58 to determine that the tissue being imaged is not ophthalmic tissue. The processor initially sets the system settings and/or transmit power to be at a level for imaging sensitive tissues and once the processor has determined that the tissue being imaged is not ophthalmic or other sensitive tissue, the processor or a user is allowed to change the system settings and/or increase the transmit power.

In some embodiments, the processor of the ultrasound system is programmed to estimate possible bio-effects of the ultrasound signals delivered to tissue using a certified model that relates the transmit voltage to one or more imaging parameters such as mechanical index (MI), thermal index (TI), and spatial peak temporal average intensity (SPTA). To prevent damage to sensitive tissue, the processor uses the model to determine the correct transmit voltage that will not exceed a recommended value for any of these parameters. To prevent damage to sensitive tissue, the processor detects that sensitive tissue is being imaged and alerts the user to confirm that the parameter values are safe for such tissues. Alternatively, the processor selects the parameter values that are safe for such tissues or can set the parameters to have values that are safe for such tissues until it is confirmed that such sensitive tissues are not being imaged. In other embodiments, some imaging modes (e.g. color Doppler) that require higher energy transmissions than B-mode or M-mode imaging are not enabled until it is confirmed such imaging modes are safe for the tissue type being examined.

Figure 3:
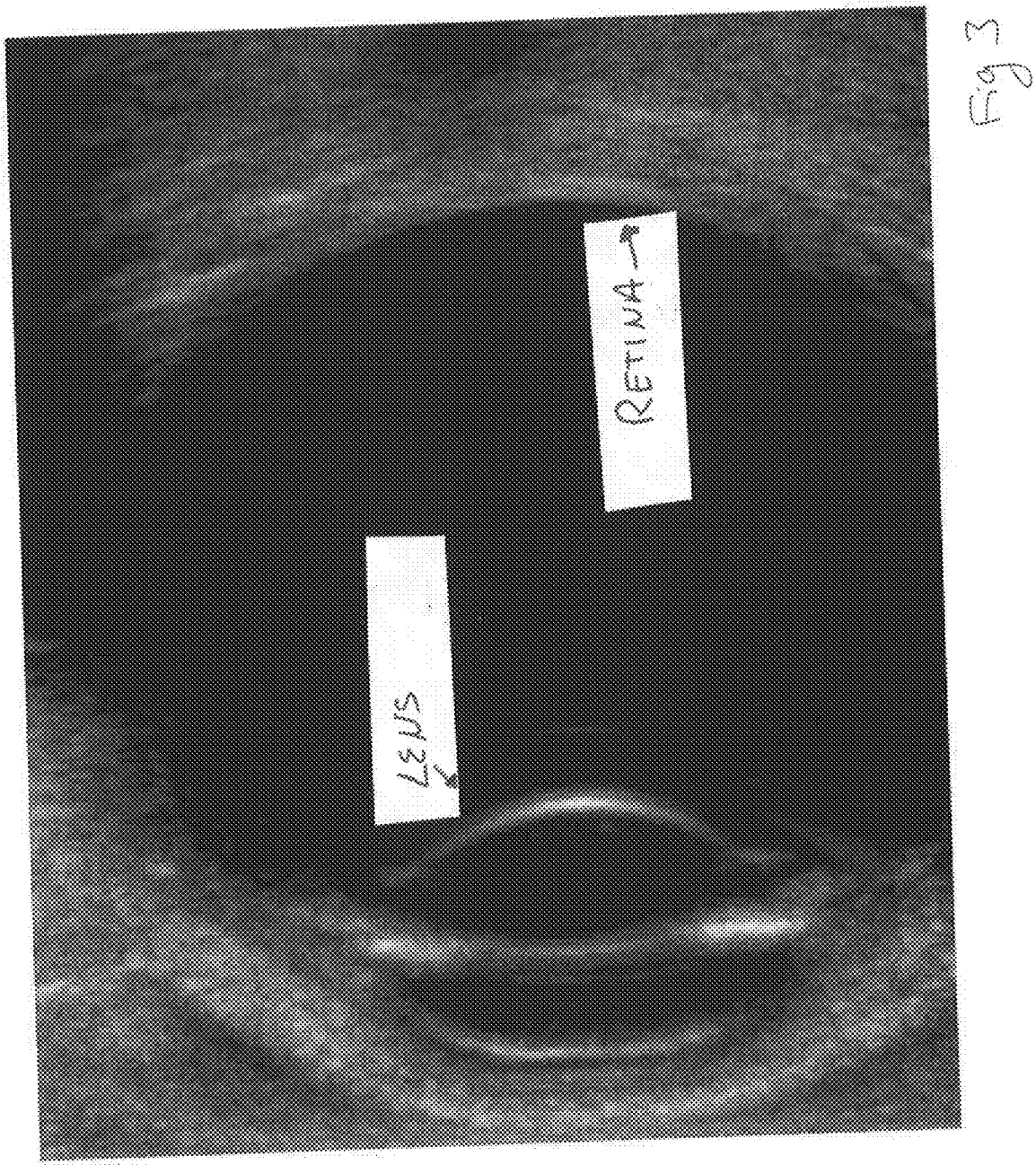
FIG. 3 illustrates a typical ultrasound image of eye tissue.

FIG. 3 illustrates a typical ultrasound image of an eye. Various anatomical features in the image can be seen as bright areas compared with the low intensity (e.g. black) regions from which little echo signal is received. Two features that are easily detectable in the image are the rear surface of the lens and the retina. In most humans, these shapes tend to be fairly regular and of a generally uniform size. Therefore, in one embodiment, the processor (or DSP or graphics processor) is programmed to analyze an image produced by the graphics processor to detect the presence or absence of one or more of these features. If one or more of these features is present, then the processor is programmed to classify the tissue as likely being ophthalmic. If these features are not present, then the processor can classify the tissue as likely not being ophthalmic. In some embodiments, a full resolution image that is suitable for diagnostics is analyzed to detect the presence of sensitive tissues. In another embodiment, an image is produced with less resolution (e.g. from fewer scanlines) in order to speed processing. In some embodiments, multiple images may be analyzed and combined to detect the presence of sensitive tissue.

FIG. 4 shows one method of identifying ophthalmic tissue. In this case, the processor is programmed to analyze the brightness of the pixels that comprise the image to identify structures that may represent a lens and a retina. In some embodiments, the processor analyzes the pixel intensities and/or pixel gradients to locate bright pixels that are nearby corresponding dark pixels. The processor is programmed to identify a set of pixel points (L) that may represent a lens and an additional set of pixel points (R) that may represent a retina. On a two-dimensional image, each pixel point has a corresponding X,Y coordinate pair (or set of polar coordinates). In one embodiment, the processor is programmed to fit a curve to the sets of coordinates and to analyze the curves to determine what anatomical object the curves likely represent. In one embodiment, the processor is programmed to analyze the curve representing the set of points L to determine for example, the distance of the curve away from the transducer and its radius. If these values fall within a range typically associated with a lens of an eye, then the computer can determine that the set of points likely represents a lens. In one embodiment, similar steps are performed on the set of points R to determine if the set of points likely represents a retina. In some embodiments, other measurements such as one or more of the distance D1 between the transducer and the set of points L, the distance D2 between the transducer and the set of points R and the distance D3 between the set of points L and the set of points R can be analyzed to determine if these values fall within ranges typically associated with the human eye.

Other techniques such as comparing a new ultrasound image produced by the image processor 58 with one more ultrasound images stored in a database memory 70 that are known to represent eye scans can be performed using for example, a sum of differences squared or other image comparison algorithms. Other algorithms as used in facial recognition for example, can be used to compare an image of the tissue with known images of ophthalmic tissues or other sensitive tissues (e.g. fetal images). In the case of other sensitive tissues like fetal tissues, the processor 40 (or DSP or GPU) is programmed to analyze images for pixels that represent features commonly found in such tissues or to compare against fetal images using image comparison algorithms.

Once it is determined that the tissue that was imaged likely is or is not ophthalmic tissue, the system settings can be changed or the energy of the acoustic signals that are produced by the transducer can be adjusted down if the energy is too high or up if it is safe to do so.

Although the above description is described with respect to human ophthalmic tissues, it will be appreciated that the eyes of animals (cats, dogs, horses etc.) are similar enough that the same type of analysis can be performed if the ultrasound imaging system is designed to be used in a veterinary setting. Similarly, other ultrasound images can be analyzed for the presence of other sensitive tissues, such as fetal tissue. Similarly, the ultrasound images can be analyzed by the processor to confirm the absence of such sensitive tissues before allowing the transmit power to be increased.

In some embodiments, if the processor detects the presence of such tissue, the processor is programmed to trigger an alarm (e.g. visual on the display screen 60, audible on a speaker that is part of the I/O 74 or a tactile alarm such a vibration) to alert the operator to confirm that the system settings are correct and/or that the power level is appropriate for the type of tissue being imaged. In other embodiments, the processor is programmed to change the system settings or reduce the transmit power under program control. In still other embodiments, the processor is programmed to begin imaging with system settings that are correct for sensitive tissue at a power level that is safe for such sensitive tissues and to prevent the power level from being increased until such time as it is determined that such sensitive tissue is not being imaged.

In some embodiments, other mechanisms are used to identify the tissue being imaged. For example, the ultrasound transducer can be equipped with a camera 80 (FIG. 2) similar to those commonly found on cellular telephones or with an infrared camera. A camera control chip 82 is controlled by the processor to interact with the camera 80 and produce black and white or color images. The output of the camera control chip can be supplied to the image processor 58, to the processor 40 or can be stored in a memory. Images obtained with the camera can be analyzed with feature or pattern recognition software algorithms to identify the tissue to be imaged with the ultrasound imaging machine. For example, if the camera obtains an image of tissue before the ultrasound signals are applied, the processor may be programmed to analyze the image for the presence of a circle of dark pixels (e.g. the pupil) surrounded by colored pixels (the iris). If an image contains these features, the processor can adjust the system settings and/or the power of the acoustic signals produced by the transducer to be safe for ophthalmic tissues.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. An ultrasound imaging system comprising:
   an image processor that is configured to produce an image of tissue being examined from received ultrasound signals; and
   a processor that is configured to:
   begin imaging by producing ultrasound signals that are safe for sensitive tissues;
   analyze the image to determine if the tissue being imaged is sensitive tissue;
   in response to determining that the tissue being imaged is sensitive tissue confirm that the energy delivered by the ultrasound imaging system is safe for imaging such sensitive tissue; and
   in response to determining that the tissue being imaged is not sensitive tissue increase the transmit power level of the ultrasound signals.

2. The ultrasound imaging system of claim 1, wherein the sensitive tissue is ophthalmic tissue.

3. The ultrasound imaging system of claim 2, wherein the processor is configured to analyze the image of the tissue for the presence of anatomical structures present in an eye.

4. The ultrasound imaging system of claim 1, wherein the sensitive tissue is fetal tissue.

5. The ultrasound imaging system of claim 1, wherein the processor is configured to confirm that the energy delivered is safe for the sensitive tissue by producing an alert to a user to confirm that one or more system settings are correct for imaging the sensitive tissue.

6. The ultrasound imaging system of claim 1, wherein the processor is configured to confirm that the energy delivered is safe for sensitive tissue by reducing the transmit power of ultrasound signals produced.

7. The ultrasound imaging system of claim 6, wherein the processor is configured to control the power level of the ultrasound signals produced by controlling a maximum transmit voltage of the ultrasound signals.

8. The ultrasound imaging system of claim 6, wherein the processor is configured to control the power level of the ultrasound signals produced by controlling a duty cycle of the ultrasound signals.

9. The ultrasound imaging system of claim 6, wherein the processor is configured to control the power level of the ultrasound signals produced by controlling a number of transmit elements in a transducer that produce the ultrasound signals.

10. The ultrasound imaging system of claim 2, wherein the processor is configured to compare the image produced by the image processor with one or more ultrasound images known to represent ophthalmic tissue.

11. The ultrasound imaging system of claim 2, wherein the processor is configured analyze the image produced by the image processor for a representation of one or more anatomical features known to be present in an eye.

12. An ultrasound imaging system comprising:
    an image processor that is configured to produce an image of tissue being examined; and
    a processor that is configured to:
    begin imaging by producing ultrasound signals that are safe for sensitive tissues;
    analyze an image of the tissue being examined to determine if the tissue being imaged is sensitive tissue;
    in response to determining that the tissue being imaged is sensitive tissue confirm that a level of energy delivered to the tissue by ultrasound signals produced by the ultrasound imaging system is appropriate for imaging sensitive tissue; and
    in response to determining that the tissue being imaged is not sensitive tissue increase the transmit power level of the ultrasound signals.

13. The ultrasound imaging system of claim 12, wherein the processor is configured to produce an alarm that requests that a user confirm that one or more settings of the ultrasound system are appropriate for imaging sensitive tissues.

14. The ultrasound imaging system of claim 12, wherein the sensitive tissue is ophthalmic tissue.

15. The ultrasound imaging system of claim 12, wherein the sensitive tissue is fetal tissue.

16. The ultrasound imaging system of claim 12, wherein the processor is configured to analyze an image produced by a camera on an ultrasound probe.

17. The ultrasound imaging system of claim 12, wherein the processor is configured to analyze an image produced from echo signals received by an ultrasound probe.

* * * * *